(12) United States Patent
Baker et al.

(10) Patent No.: US 6,558,422 B1
(45) Date of Patent: May 6, 2003

(54) STRUCTURES HAVING COATED INDENTATIONS

(75) Inventors: Aaron B. Baker, Richland, WA (US); Joan E. Sanders, Kirkland, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/532,855

(22) Filed: Mar. 22, 2000

Related U.S. Application Data

(60) Provisional application No. 60/126,545, filed on Mar. 26, 1999.

(51) Int. Cl.[7] ................................................. A61F 2/02
(52) U.S. Cl. ................... 623/16.11; 424/422; 623/1.42; 623/23.5; 623/23.74
(58) Field of Search .................... 428/137, 131, 428/163, 34.1, 35.7, 172; 424/422; 623/16.11, 23.74, 23.76; 427/261, 2.24

(56) References Cited

U.S. PATENT DOCUMENTS

| | | | | |
|---|---|---|---|---|
| 4,752,294 A | * | 6/1988 | Lundgren ................. | 623/23.74 |
| 4,795,472 A | * | 1/1989 | Crowninshield et al. . | 623/23.74 |
| 5,271,736 A | * | 12/1993 | Picha ....................... | 623/23.74 |
| 5,308,576 A | * | 5/1994 | Green et al. ................... | 419/38 |
| 5,418,833 A | * | 5/1995 | Logan ......................... | 378/154 |
| 5,976,826 A | * | 11/1999 | Singhvi et al. ............... | 435/29 |
| 6,106,558 A | * | 8/2000 | Picha ....................... | 623/23.74 |
| 6,236,111 B1 | * | 5/2001 | Legay et al. ................ | 257/730 |
| 6,379,385 B1 | * | 4/2002 | Kalas et al. ............. | 623/17.11 |
| 6,440,444 B2 | * | 8/2002 | Boyce et al. ................ | 424/422 |

OTHER PUBLICATIONS

Niino, H et al., "Surface modification and metallization of fluorocarbon polymers y excimer laser processing," *Appl Phys Lett*, 63(25):3527–3529 (1993).

Favia, P. et al., "Surface Chemical Composition and Fibrinogen Adsorption–retention of Fluoropolymer Films Deposited from and RF Glow Discharge," *Plasmas and Polymers*, 1(4):299–326 (1996).

Lee, K.W. et al., "Surface–Selective Hydroxylation of Polypropylene," *Macromolecules*, 21(2):309–313 (1988).

Bamford, C.H. et al. "Studies in polymer surface functionalization and grafting for biomedical and other applications," *Polymer*, 35(13):2844–2852 (1994).

Sano, S. et al., "Introduction of functional groups onto the surface of polyethylene for protein immobilization," *Biomaterials* 14(11):817–822 (1993).

* cited by examiner

*Primary Examiner*—David H. Willse
*Assistant Examiner*—Suzette J. Jackson
(74) *Attorney, Agent, or Firm*—Christensen O'Connor Johnson Kindness PLLC

(57) ABSTRACT

In one aspect the present invention provides indented structures that each include (a) a body defining a plurality of indentations, substantially all of the plurality of indentations including a surface layer including a biologically active substance; and (b) a body surface, wherein each of the plurality of indentations opens onto the body surface through a plurality of openings, and wherein the biologically active substance is not substantially present on the body surface. Examples of structures of the present invention include medical devices, such as medical devices that are completely or partially implantable into a living body. The surface layer of the indentations (or at least some of the indentations) of the medical devices of the invention may include biologically active molecules, such as proteins, that promote the growth of cells into and/or within the indentations, thereby promoting the acceptance of the implanted device by the living body. In another aspect, the present invention provides methods for making indented structures.

12 Claims, 6 Drawing Sheets

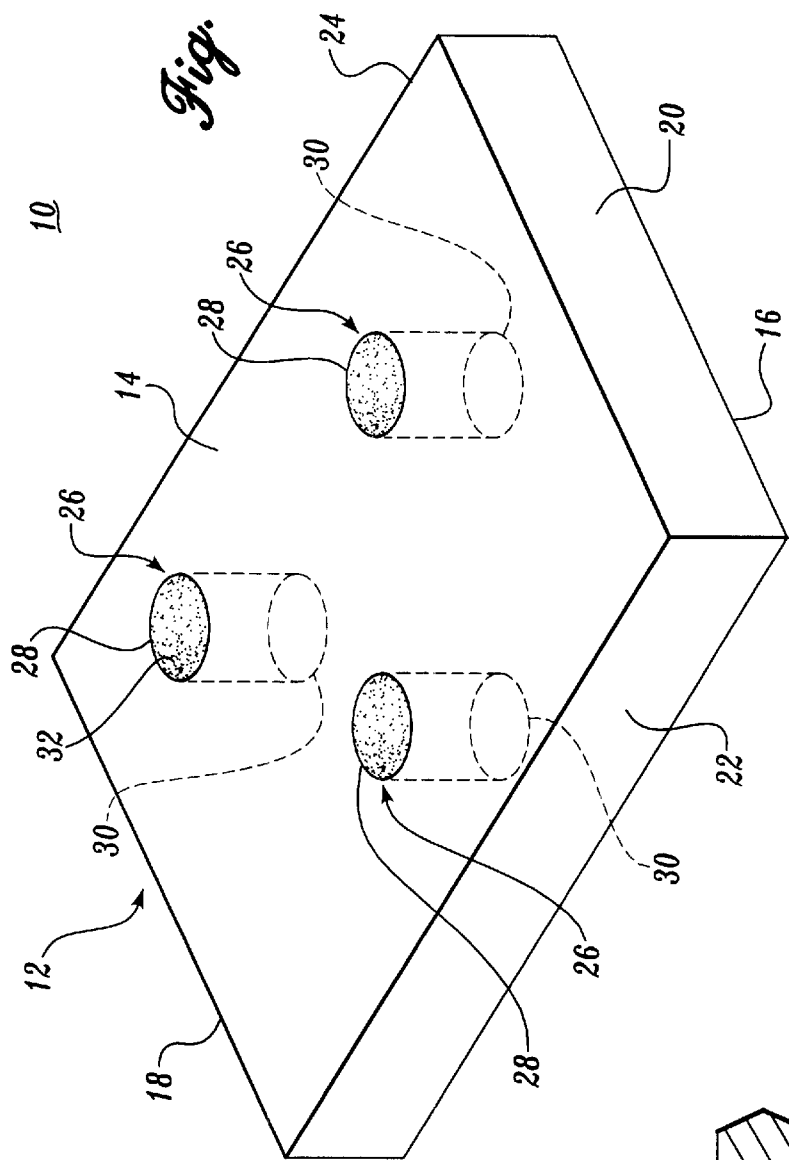
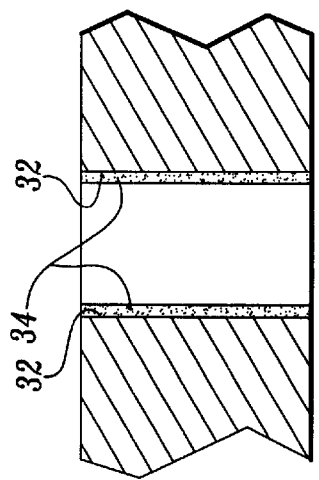

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (1)..(4)
<223> OTHER INFORMATION: four amino acid fragment of SPARC protein

<400> SEQUENCE: 1

Lys Gly His Lys
  1
```

STRUCTURES HAVING COATED INDENTATIONS

RELATED APPLICATIONS

The present application claims benefit of priority of provisional patent application serial No. 60/126,545, filed Mar. 26, 1999.

FEDERAL GOVERNMENT FUNDING

This invention was made with government support under grant number 9872882 awarded by the National Science Foundation. The government has certain rights in the invention.

FIELD OF THE INVENTION

The present invention is related to structures, such as implantable medical devices, that have an indented surface, and methods for making the same.

BACKGROUND OF THE INVENTION

The present invention provides biomedical structures, and methods for their manufacture, having indentations that are selectively coated with a substance having a desirable property, such as a substance possessing a desired biological activity. For example, medical devices that are implanted into an animal body, such as the human body, often stimulate a so-called "foreign body reaction" which produces a fibrous capsule around the implanted device. The fibrous capsule impedes vascular communication between the body and the implanted device leading to additional, fibrous encapsulation that reduces the effectiveness and working life of the device. Thus, for example, there is a need for implantable, medical devices that have one or more surfaces adapted to promote cellular communication (such as vascularization) with the cells of the body into which the medical device is implanted.

SUMMARY OF THE INVENTION

In one aspect the present invention provides indented structures (such as biomedical structures) comprising indentations that are coated with at least one biologically active substance. The indented structures of the invention each comprise (a) a body defining a plurality of indentations, substantially all of the plurality of indentations comprising a surface layer comprising a biologically active substance; and (b) a body surface, wherein each of the plurality of indentations opens onto the body surface through a plurality of openings, and wherein the biologically active substance is not substantially present on the body surface. Examples of structures of the present invention include medical devices (such as devices that provide substrates and/or frameworks for culturing cells, tissues or organs in vitro or in vivo), including medical devices that are completely or partially implantable into a living body. The surface layer of the indentations (or at least some of the indentations) of the medical devices of the invention may comprise biologically active substances, such as proteins, that promote the growth of cells into and/or within the indentations, thereby promoting the acceptance of the implanted device by the living body, or achieve some other desired response.

In another aspect, the present invention provides methods for making indented structures (such as biomedical structures) comprising indentations that are coated with at least one biologically active substance. The methods of this aspect of the invention include the steps of (a) treating a structure, comprising a body and a body surface, to form a plurality of indentations in the body, each of the plurality of indentations (1) opening onto the body surface through a plurality of openings, and (2) further defining an indentation surface; and (b) forming a layer on at least some of the indentation surfaces, the layer comprising a biologically active substance, provided that the layer is not formed on a substantial portion of the body surface. The methods of the invention can be used, for example, to make medical devices (completely or partially implantable into a living body) comprising indentations wherein the indentations (or a portion thereof) are coated with one or more biologically active substances, such as proteins, that enhance a desired biological reaction in use, such as promotion of the growth of cells into and/or within the indentations, thereby promoting the acceptance of the device by the living body.

As more fully discussed herein, the structures and methods of the present invention can be used in any situation where there is a need to stimulate the growth of specific cell, tissue and/or organ types, or to promote some other biological function. For example, structures of the invention can be used to promote vascular communication between an implanted medical device and the surrounding tissue.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 shows a perspective view of an indented structure of the invention.

FIG. 2 shows a cross-section of an indentation defined by an indented structure of the invention.

DETAILED DESCRIPTION OF THE PREFERRED EMBODIMENT

In one aspect the present invention provides indented structures that each comprise (a) a body defining a plurality of indentations, substantially all of the plurality of indentations comprising a surface layer comprising a biologically active substance; and (b) a body surface, wherein each of the plurality of indentations opens onto the body surface through a plurality of openings, and wherein the biologically active substance is not substantially present on the body surface.

The phrase "substantially all of the plurality of indentations comprising a surface layer comprising a biologically active substance", and grammatical equivalents thereof, means more than 50% of the indentations, preferably more than 75% of the indentations, more preferably more than 90% of the indentations, and most preferably more than 99% of the indentations comprise a surface layer comprising a biologically active substance. In one embodiment of the indented structures of the invention, 100% of the plurality of indentations comprise a surface layer comprising a biologically active substance.

The phrase "the biologically active substance is not substantially present on the body surface", and grammatical equivalents thereof, means that less than 50%, preferably less than 25%, more preferably less than 10%, and most preferably less than 1% of the amount of biologically active substance(s) present in and/or on the indented structure is present on the body surface. In one embodiment of the indented structures of the invention, the body surface of the indented structure comprises less than 0.5% of the biologically active substance present in the structure. Typically, biologically active substance(s) present in the indentation surface layer is covalently attached thereto, while biologically active substance(s) present on the body surface is non-covalently attached thereto.

Figure 3:
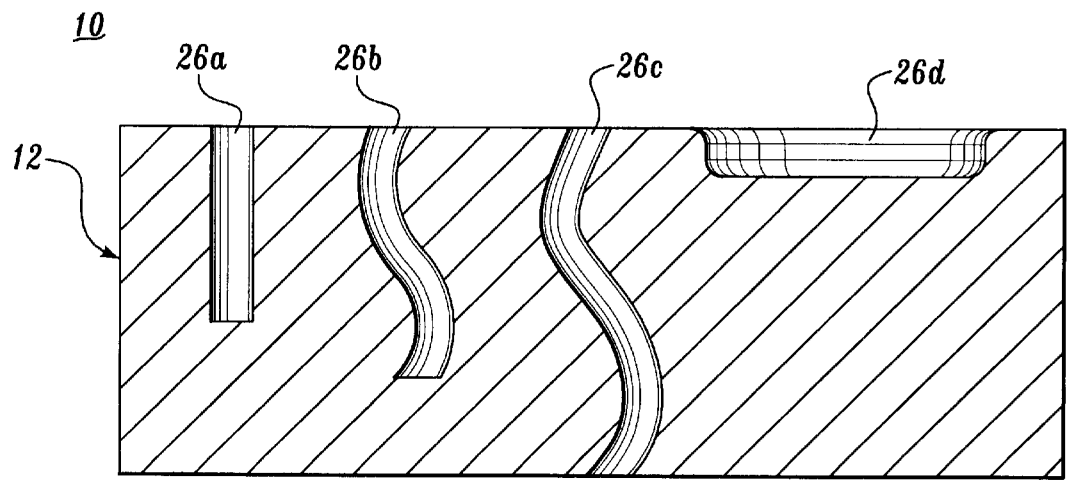
FIG. 3 shows a cross-section of an indented structure of the invention that includes several representative configurations of indentations.

As used herein, the term "indentation", or "indentations", includes indentations that partially penetrate a structure, and indentations that penetrate all the way through a structure (as exemplified in FIG. 3 herein).

As used herein, the phrase "a medical device", and grammatical equivalents thereof, means a device that is completely or partially implanted into a living body during the course of normal operation of the device.

FIG. 1 shows one embodiment of the indented structures of the present invention wherein indented structure 10 comprises a body 12 having an upper surface 14, a lower surface 16, a first end 18, a second end 20, a first face 22 and a second face 24. In the embodiment shown in FIG. 1, structure body 12 defines a plurality of indentations 26 which extend from upper surface 14 to lower surface 16 and completely penetrate structure body 12, each of indentations 26 comprising a first opening 28, defined by upper surface 14, a second opening 30, defined by lower surface 16, and an indentation surface 32. As shown more clearly in FIG. 2, indentation surface 32 is coated with a layer 34 that comprises at least one type of biologically active substance, such as a biologically active protein or peptide.

Figure 4:
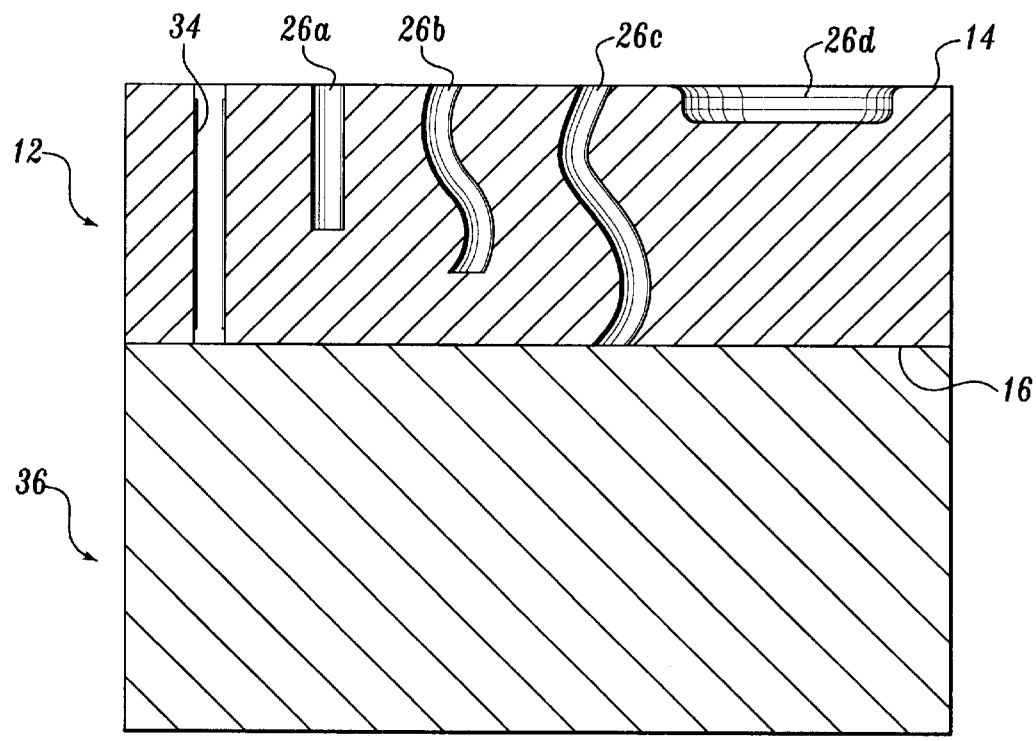
FIG. 4 shows a cross-section of an indented structure of the invention attached to a substrate structure.

Indentations 26 can have a variety of configurations in addition to the columnar configuration shown in FIG. 1 that completely penetrates structure body 12. FIGS. 3 and 4 show other, representative examples of acceptable configurations of indentations 26, including: indentation 26a that is a columnar configuration that partially penetrates structure body 12, indentation 26b that is a curved configuration that partially penetrates structure body 12, indentation 26c that is a curved configuration that completely penetrates structure body 12 and indentation 26d that is a groove defined by body 12. Indentations 26 can penetrate structure body 12 at any desired angle.

Layer 34 on indentation surface 32 can comprise any biologically active substance, or combinations thereof. Representative examples of biologically active substances that can be used to form layer 34 include, but are not limited to: growth factors (such as fibroblast growth factors, platelet derived growth factors, transforming growth factors, insulin-like growth factors, nerve growth factors, vascular endothelial growth factors, hematopoietic growth factors and epidermal growth factors); stimulators of vasculogenesis (i.e., stimulate the formation of new blood vessels) including vascular growth factors, angiogenin, and osteonectin; stimulators of the growth of other types of tissue, such as epidermal growth factor and bone morphogenic proteins; extracellular matrix proteins, such as collagens, thrombospondins, osteopontin, osteonectin, vitronectins, laminins, or one or more functional domains of the foregoing proteins. Representative examples of useful functional domains include cellular attachment domains that recognize cell-surface molecules, such as integrins. Additionally, biologically active fragments of molecules such as elastin, glycosaminoglycans (such as hyaluronic acid) and dermatan sulfate, can be used to form layer 34. Non-protein, biologically active molecules that can be used to form layer 34 include antibiotics, drugs utilized to treat diabetes and antisense oligonucleotides.

Thus, for example, layer 34 of indentation surface 32 can include one or more stimulators of vasculogenesis that promote the growth of blood vessels into and/or within indentations 26, thereby reducing the tendency of the surrounding tissue (when structure 10 is implanted into a living body) to mount a foreign body reaction. In some embodiments of indented structures 10 of the invention, some indentations 26 are coated with one or more types of biologically active substance(s), while other indentations 26 are coated with different types of biologically active substance(s).

Layer 34 covers at least a portion of indentation surface 32 of at least some of indentations 26. Layer 34 may cover all of indentation surface 32 of all of indentations 26. In this context, the term "cover all of indentation surface 32" means that greater than 95%, preferably greater than 98%, more preferably greater than 99%, most preferably 100% of the surface area of indentation surface 32 is covered with layer 34. Additionally, in this context, the term "all of indentations 26" means greater than 95%, more preferably greater than 98%, most preferably 100% of indentations 26 include layer 34.

In one embodiment, indentations 26 have an average, maximum diameter in the range of from about 1 micron to about 100 microns, more preferably about 50 microns, and penetrate structure 10 to a depth of from about 1 micron to about 2 millimeters, more preferably from about 1 micron to about 500 microns.

Indented structures 10 can be made from any suitable material, including polymers, metals and composites. Representative examples of polymers useful for making structures 10 include, but are not limited to: polypropylene, polyethylene, polyurethane, polyester, polytetrafluoroethylene (PTFE), poly(lactic acid), poly(glycolic acid), polystyrene, polycarbonate, polyethylene glycol (PEG), fluoropolymers, collagen, poly(galactic acid), polyethylene terephthalate (PET), poly(dioxanone), poly(trimethylene carbonate) copolymers, poly (ε-caprolactone) homopolymers and copolymers, polyanhydrides, polyorthoesters, and copolymers of any of the foregoing. Representative examples of metals useful for making indented structures 10 include, but are not limited to: steel, titanium and NiTi smart materials (such as the materials described in Miyazaki, S., et al., Proc. Int'l Soc. Optical Engineering, 2716: 95–103 (1996)). Representative examples of composites useful for making structures 10 include, but are not limited to: hydroxyapatite and Bioglass® (such as the Bioglass® materials disclosed in Ducheyne, P., J. Biomedical Materials Research, 19(3): 273–291 (1985), which publication is incorporated herein by reference).

Indented structures 10 of the present invention include medical devices that are adapted to be implanted into a living body, such as a mammalian body, including a human body. Some implantable, medical devices are completely implanted into a living body (i.e., the entire device is implanted within a living body), while some implantable, medical devices are partially implanted into a body (i.e., only part of the device is implanted within a living body, the remainder of the device being located outside of the living body). Further, some implantable, medical devices include both living tissue and non-living material. Representative examples of implantable medical devices include, but are not limited to: prosthetic devices (such as artificial hip joints and artificial knee joints), cardiovascular devices (such as vascular grafts and stents), skin substitutes (such as dermal and epidermal scaffolds), scaffolds that support tissue growth (in such anatomical structures as bone, tooth, nerves, pancreas, eye and muscle), implantable biosensors (such as those used to monitor the level of drugs within a living body, or the level of blood glucose in a diabetic patient) and percutaneous devices (such as catheters) that penetrate the skin and link a living body to a medical device, such as a kidney dialysis machine. Examples of partially implanted medical devices include catheters and skin substitutes. Examples of medical devices that are completely implanted into a living body include stents and artificial hip joints.

In some embodiments of the present invention, indented structures 10 are attached to a substrate structure, such as a medical device. For example, FIG. 4 shows a cross-section of an embodiment of indented structures 10 of the present invention wherein indented structure 10 includes body 12 defining a plurality of indentations 26 which can have numerous conformations, such as the representative conformations 26*a*, 26*b*, 26*c* and 26*d*. Indented structure 12 also includes upper surface 14 and lower surface 16. In the embodiment shown in FIG. 4, lower surface 16 of indented structure 12 is fixedly attached (such as by an adhesive) to a substrate structure 36. Again, indentations 26 (and all conformations thereof) are at least partially coated with layer 34 that includes at least one type of biologically active substance. In this embodiment of the indented structures 10 of the present invention, indented structure 10 may first be indented, and layer 34 applied to indentation surface 32, before affixing, or otherwise attaching, indented structure 10 to substrate structure 36; or indented structure 10 may be formed in situ on substrate structure 36. Substrate structure 36 can be a medical device, such as the medical devices mentioned herein.

Figure 5:
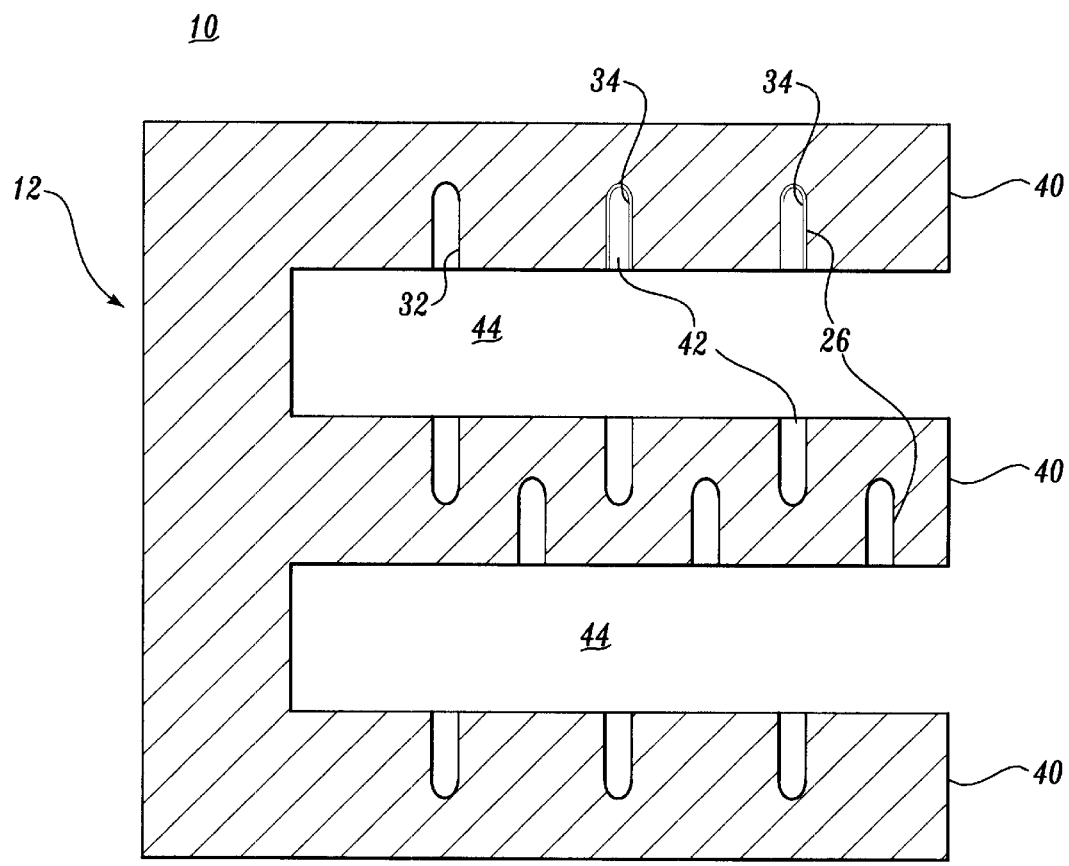
FIG. 5 shows a cross-section of an indented structure of the invention that includes several body layers.

As shown in FIG. 5, in another embodiment of the indented structures 10 of the invention, indented structure 10 includes body 12 defining a plurality of body layers 40 that each define a plurality of indentations 26 that each include an opening 42. Each of the indentations 26 define an indentation surface 32, and at least some of indentation surfaces 32 are coated with a layer 34 that includes at least one type of biologically active substance. Plurality of body layers 40 define a plurality of cavities 44 therebetween. If the material chosen to fabricate body layers 40 is flexible, then the dimensions of cavities 44 can vary depending the relative locations of each body layer 40. In operation, living cells grow into cavities 44 and penetrate indentations 26, thereby physically securing indented structure 10 within a living body. This embodiment of structures 10 of the invention can be used, for example, to form a skirt around a percutaneous device (such as a catheter) thereby promoting growth of skin cells and tissue into structure 10.

In another aspect, the present invention provides methods for making indented structures (such as biomedical structures). The methods of the invention include the steps of (a) treating a structure, comprising a body and a body surface, to form a plurality of indentations in the body, each of the plurality of indentations (1) opening onto the body surface through a plurality of openings, and (2) further defining an indentation surface; and (b) forming a layer on at least some of the indentation surfaces, the layer comprising a biologically active substance, provided that the layer is not formed on a substantial portion of the body surface.

The phrase "forming a layer on at least some of the indentation surfaces", and grammatical equivalents thereof, means that the layer is formed on at least 50% of the indentation surfaces, preferably on at least 75% of the indentation surfaces, more preferably on at least 90% of the indentation surfaces, most preferably on at least 99% of the indentation surfaces. In one embodiment of the methods of the invention, the layer is formed on 100% of the plurality of indentations. The layer preferably covers greater than 95%, more preferably greater than 98%, most preferably greater than 99% of the surface area of the indentation surfaces.

The phrase "provided that the layer is not formed on a substantial portion of the body surface" means that the layer is formed on less than 5%, preferably less than 2%, more preferably less than 1%, most preferably less than 0.1% of the area of the body surface. In one embodiment of the methods of the invention, the layer is not formed on any portion of the body surface. Typically, in indented structures 10 formed in accordance with the methods of the invention, biologically active substances present in the indentation surface layer are covalently attached thereto, while biologically active substance present on the body surface is non-covalently attached thereto.

Figure 6A:
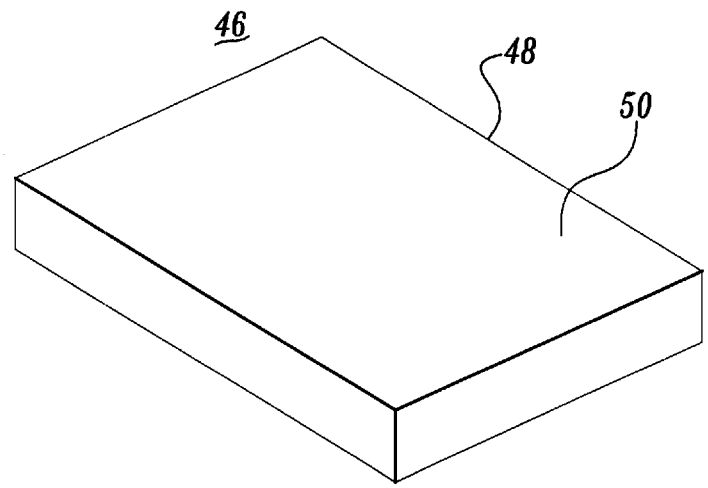
FIG. 6A shows a substrate that can be treated in accordance with the methods of the invention to form an indented structure of the invention.
Figure 6B:
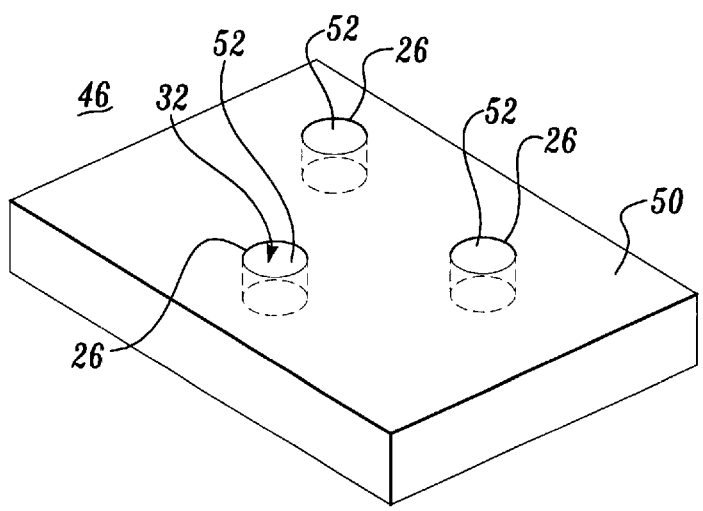
FIG. 6B shows the substrate of FIG. 6A which has been treated to form a plurality of indentations.
Figure 6C:
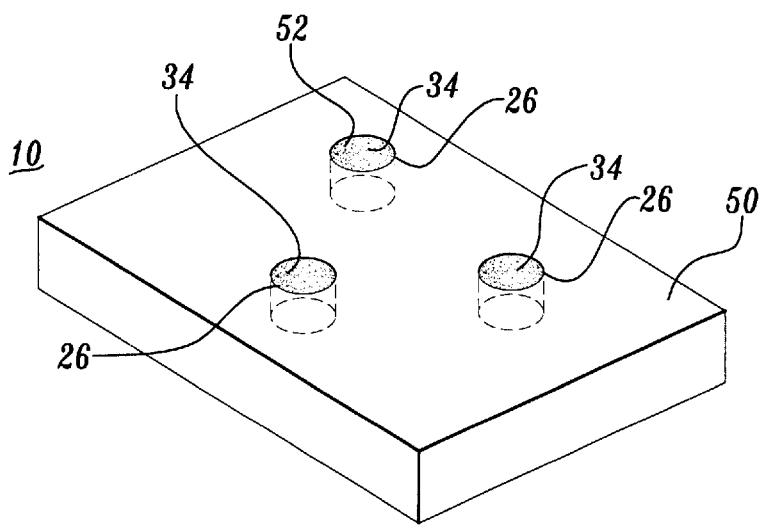
FIG. 6C shows the treated substrate of FIG. 6B wherein the surface of the indentations have been coated with a layer comprising at least one biologically active substance.

As shown for example in FIG. 6A, in the practice of the methods of the invention, indented structure 10 is made from a structure 46, comprising a body 48 defining a surface 50. As shown in FIG. 6B, structure 46 is treated to form a plurality of indentations 26 (that partially penetrate body 48 in the embodiment shown in FIG. 6) that each comprises an opening 52 and defines indentation surface 32 which has a surface chemistry that permits attachment, preferably covalent attachment, of one or more biologically active substances to indentation surfaces 32. As shown in FIG. 6C, layer 34 is then formed on indentation surfaces 32 and comprises one or more substances, such as proteins, having desired biological activity or activities. Layer 34 is not formed on a substantial portion of structure surface 50. Preferably none of the biologically active substance(s) present in layer 34 are present on structure surface 50, and if any of the aforementioned, biologically active substance(s) are present on structure surface 50, they are preferably not covalently bound to structure surface 50.

Structure 46 can be in any physical form (such as a tube, disk or film), and can be made using any art-recognized technique from any biodegradable or non-biodegradable substance, such as polymers, or combinations thereof. Representative examples of polymers useful for making structure 46 include, but are not limited to: polypropylene, polyethylene, polyurethane, polyester, polytetrafluoroethylene (PTFE), poly(lactic acid), poly(glycolic acid), polystyrene, polycarbonate, polyethylene glycol (PEG), fluoropolymers, collagen, poly(galactic acid), polyethylene terephthalate (PET), poly(dioxanone), poly(trimethylene carbonate) copolymers, poly ($\epsilon$-caprolactone) homopolymers and copolymers, polyanhydrides, polyorthoesters, and copolymers of any of the foregoing. Representative examples of metals useful for making structure 46 include, but are not limited to: steel, titanium and NiTi smart materials. Representative examples of composites useful for making structure 46 include, but are not limited to: hydroxyapatite and Bioglass®. Structure 46 can be a device, such as a medical device, such as the medical devices mentioned supra.

Indentations 26 can be formed by a variety of means, including, but not limited to, the use of one or more lasers, chemical etching, corrosion, micromechanical machining, polymerization, casting processes, the use of nanotubes, co-polymerization with extractable, solid materials or other removable structures (such as liposomes and soluble crystals). In one embodiment of the chemical etching technique, an inert, perforated sheet is placed over structure 46 which is then placed in an etching solution that etches the portion of structure 46 that is exposed by the perforations in the overlying material. Similarly, the technique of photo-etching (commonly used in microchip fabrication) can be used to form indentations 26. Additionally, structure 46 (and the overlying, perforated sheet) can be immersed in a corrosive solution that corrodes the portion of structure 46 that is exposed by the perforations in the overlying material.

Micromechanical machining utilizes fine machining implements, such as needles and microdrill bits, to form indentations 26 by machining structure 46 in a manner similar to conventional machining. In other techniques, indentations 26 can be formed in structure 46 by casting or polymerizing the material from which structure 46 is made in a mold that creates indentations 26. Nanotubes can be included in the material from which structure 46 is made when the material is polymerized or cast. These tubes can then either be removed to create indentations 26, or, if hollow, open-ended nanotubes are used, they can be left in the material to form indentations 26. Other types of material or polymer can be included in the casting or polymerization of the material used to make structure 46, and then removed after the process was finished. This would leave imprints of the objects in structure 46 thereby forming indentations 26. Indentations 26 can also be created in structure 46 by electrospinning (i.e., applying a voltage to a stream or drop of polymer) the material from which structure 46 is made.

The presently preferred method for making indentations 26 is with a laser, such as an ultraviolet (U.V.) laser. Thus, for example, Niino et al. studied the effects of UV laser radiation on PTFE under atmospheres consisting of hydrazine, ammonia, and hydrogen peroxide (Niino, H. and Yabe, A., Appl Phys Lett, 63(25): 3527–3529 (1993).). They found the most effective treatment was the hydrazine atmosphere, which made the PTFE hydrophilic enough to be chemically plated with nickel metal. Example 1 herein describes the use of a pulsed LightAge alexandrite PAL-101 laser to cut squares of polyurethane and polypropylene.

As previously described with reference to indented structures 10 of the present invention (and as exemplified in FIG. 3), indentations 26 can have numerous conformations (such as columnar or curved), and may completely or incompletely penetrate indented structure 10. For example, a laser can be used to create indentations 26 having a sinusoidal conformation. In one embodiment, indentations 26 have an average, maximum diameter in the range of from about 1 micron to about 100 microns, more preferably about 50 microns, and penetrate structure 10 to a depth of from about 1 micron to about 2 millimeters, more preferably from about 1 micron to about 500 microns.

Representative examples of reactive, functional groups that can be formed on indentation surfaces 32 (and to which biologically active molecules can be attached) are aldehydes, oxides, alcohols, and acids. In some embodiments of the methods of the present invention, the process of forming indentations 26 also generates desired chemical, functional groups on indentation surface 32. For example, the use of certain types of lasers to form indentations 26 also generates functional groups on indentation surface 32 that are useful for attaching biologically active substances to indentation surface 32.

In other embodiments, the process of forming indentations 26 (such as by the use of a laser) is insufficient, by itself, to generate the desired surface chemistry on indentation surfaces 32. For example, one method of activating indentation surfaces 32 made from polypropylene or polyethylene is to use solutions of sulfuric acid/chromium(IV) oxide, nitric acid, chromium(IV) oxide, and ammonium peroxidisulfate to create oxygen-containing functional groups. Again, by way of non-limiting example, treatment with chromium(IV) oxide followed by reduction with borane can be used to generate hydroxyl groups on indentation surfaces 32 made from polypropylene or polyethylene. Other methods of activating indentation surfaces 32 include the following (and combinations thereof): isolated treatment, via photomasking, of indentation surfaces 32 with reactive chemicals, photoreactive reagents, reactive gases and plasmas; indentations 26 can be created with a laser under a reactive atmosphere, such as an atmosphere containing hydrazine, reactive plasma gases, perfluorates, oxides, nitrides, hydrides or photoreactive agents; indentations 26 can be created with a laser under a chemically inert atmosphere (such as a halogen atmosphere), and either the same type of laser or a different type of laser can be used to generate the desired surface chemistry on indentation surfaces 32; a polymer can be coated with a chemically resistant coating, then indentations 26 can be formed using a laser under a chemically inert atmosphere thereby exposing indentation surfaces 32 to which a biologically active substance can be attached; and chemical groups formed on indentation surfaces 32 can be metalized, such as by the method described in Niino, H. and Yabe, A., supra, which publication is incorporated herein by reference.

Figure 7A:
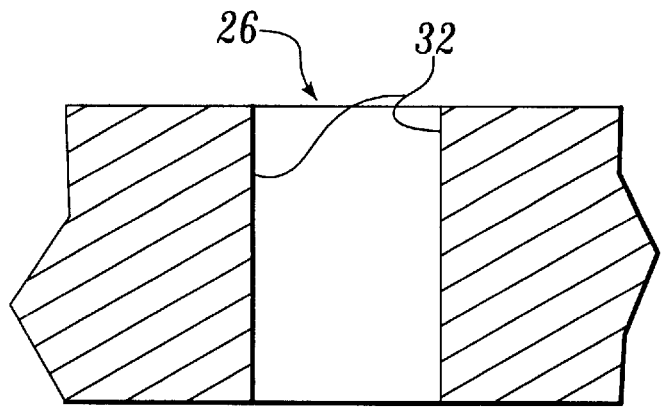
FIG. 7A shows a cross-section of an indentation defined by an indented structure of the invention.
Figure 7B:
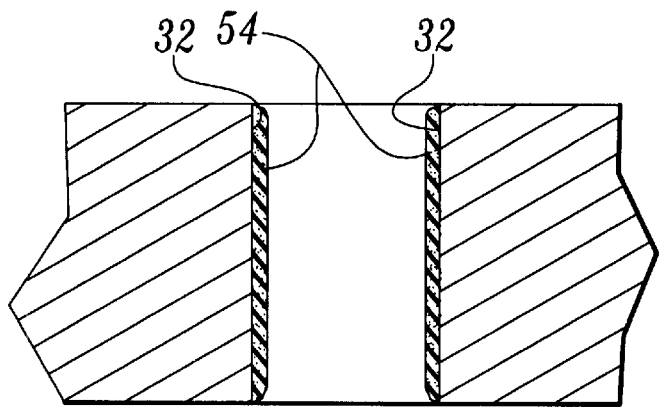
FIG. 7B shows the indentation of FIG. 7A wherein the indentation surface has been coated with a layer of polymer.
Figure 7C:
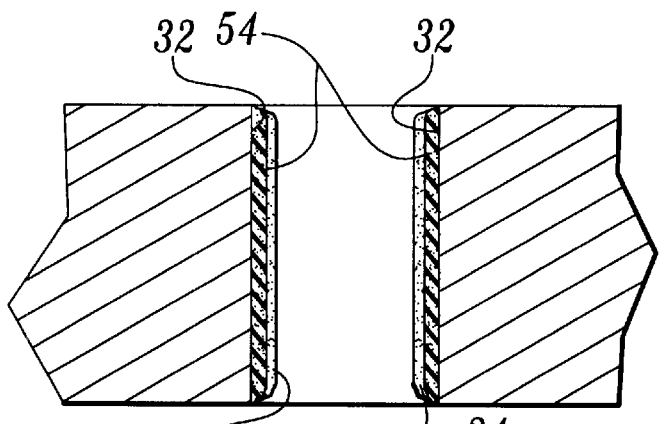
FIG. 7C shows the coated indentation of FIG. 7B wherein the polymer layer has been coated with a layer that comprises at least one biologically active substance.

As shown in FIG. 7, in one embodiment of the methods of the invention, after formation of indentations 26, including indentation surface 32, a layer of polymeric material 54, such as a layer of acrylamide, is applied to indentation surfaces 32 (see FIG. 7B). A layer 34 comprising at least one, desired, biologically active substance, or substances, is then attached to polymeric material layer 54 (see FIG. 7C), provided that polymeric material layer 54 possesses functional groups to which the biologically active substance(s) can be attached. If polymeric material layer 54 does not possess functional groups to which biologically active substances can be attached, then polymeric material layer 54 can be treated to generate such functional groups, for example as described supra and in Example 2 herein.

The methods of the invention can be used to make medical devices (completely or partially implantable into a living body) comprising indentations 26 wherein the indentations (or a portion thereof) are coated with biologically active substances, such as proteins, that promote the growth of cells into and/or within indentations 26. Further, the methods and structures of the present invention can be used in tissue engineering, i.e., to promote the growth of specific cell, tissue and organ types that can be grafted onto or implanted into a living body. By way of non-limiting example, the methods and structures of the present invention can be used to: grow tissue to patch holes and damaged portions of liver, heart, kidneys, lungs, skin, bone, cartilage, tendons, pancreas, muscles, intestines, blood vessels and neural tissue; grow tissue for tissue expansion in cosmetic surgery; to create artificial organs; grow new nervous tissue for such applications as nerve bridging, repairing spinal cord injuries, controlling the attachment of nerves to implanted sensors, controlling nerve architecture for the development of biological computing; growing new lymphatic vessels; making filters that bind specific biological molecules; making bioreactors that include specific types of cells bound to specific portions of the bioreactor.

The following examples merely illustrate the best mode now contemplated for practicing the invention, but should not be construed to limit the invention.

EXAMPLE 1

Effect of Laser Irradiation on Polymer Surface Chemistry

To examine the effects of laser cutting on polymer surface chemistry under a normal air atmosphere, several materials were cut using a pulsed LightAge alexandrite PAL-101 laser with a wavelength of 371 nm, power of 200 mJ, pulse rate of 20 Hz, and pulse length of 40 nanoseconds (ns) (performed at the facilities of the Pacific Northwest National Laboratories in Richland, Wash.). Polymer squares of polyurethane and polypropylene (3M Corporation, St. Paul, Minn.), approximately 1 cm in diameter, were cut in half using a manual laser set-up. The cut edge of the material was compared to the uncut material using ESCA. ESCA analysis showed heavy oxidation where the laser had cut the material (24% surface composition of oxygen versus 3% in the uncut material).

EXAMPLE 2

Manufacture and Implantation of Indented Structures 10

Polypropylene thin films were plasma coated with a fluoropolymer. A fluoropolymer coating was applied to polymer disks using Radio Frequency Glow Discharge (RFGD) methods (see, Favia, P., et al., Plasmas and Polymers, 1(4): 299–326 (1996), which publication is incorporated herein by reference). Polymer samples were placed on steel electrodes within a tubular glass reactor and treated for 30 seconds with argon. The samples were then exposed to a pure $C_3F_6$ glow (13.56 MHz RF, 5 W). To obtain treatment on both sides of the films, the samples were turned over, treated with argon and exposed to a $C_3F_6$ glow.

Indentations 26 were then formed in the fluoropolymer-treated samples by using a laser as follows. Laser processing was performed at Photomachining, Inc. (Pelham, N.H.) using an ESI Model 5100 Tripled Nd:YAG laser system ($\lambda$=260 nm). The system was equipped with vision, auto-alignment, and automated attenuation. All processing was performed in a certified clean room. A hexagonally-arranged array of indentations 26 was made to cover the entire surface of the polymer disks. Arrays with indentation 26 diameters of 50 microns and 100 microns were created. The samples were then cleaned ultrasonically in methanol. Only the disks with 50-micron indentations 26 were used for subsequent implantation.

The disks were then etched by treatment with chromium (IV) oxide followed by reduction with borane to yield numerous, reactive hydroxyl groups, using methods developed by Lee and McCarthy (Lee, K. W. and McCarthy, T. J., Macromolecules, 21(2): 309–313 (1988), which publication is incorporated herein by reference). In brief, following plasma and laser processing, polypropylene disks were placed in a round bottom flask and then purged with dry nitrogen for 15 minutes. A solution containing 2.0 g of chromium(IV) oxide, 20 ml of glacial acetic acid, and 20 ml acetic anhydride was added through a cannula. The solution was allowed to react at room temperature for four hours on a shaker table. The polypropylene disks were then washed sequentially in the following solutions: 1 M NaOH (2×20 ml), 1 M HCl (2×20 ml), distilled water (2×20 ml), methanol (3×20 ml), and dichloromethane (3×20 ml). The disks were then dried to constant mass at 70° C. under vacuum.

Following the oxidation reaction, the polypropylene films were placed in a dry Schlenk tube and subsequently purged with dry nitrogen for 15 minutes. Ten milliliters of THF and two milliliters of 1 M borane/THF solution were added through a cannula and the solution was allowed to react for six hours. The solution was then removed through a cannula and the disks washed in THF (4×20 ml). A solution with 10 ml of hydrogen peroxide (30% in water) and 10 ml of 3 M NaOH was allowed to react with the disks for three hours. This solution was removed and the disks were washed sequentially in distilled water (2×20 ml), 1 M HCl (3×20 ml), water (3×20 ml), methanol (3×20 ml), and dichloromethane water (3×20 ml) and dried at 70° C. under vacuum.

A polymer layer 54 of acrylamide was formed on indentation surfaces 32 by placing the disks in 100 ml of a 20% solution (w/v) of acrylamide monomer dilute nitric acid (0.04 N) in the presence of ceric ions ($2\times10^{-3}$ M from ammonium cerium (IV) nitrate). The solution was then heated to 50° C. and kept under a stream of nitrogen for three hours (Bamford, C. H. and Al-Lamee, K. G., 35(13): 2844–2852 (1994)). To remove the ungrafted homopolymer, the disks were washed with distilled water at 70° C. for 24 hours (Sano, et al., Biomaterials 14(11): 817–822 (1993)).

Hofmann degradation of the surface grafted polyacrylamide 54 (to create surface amine groups) was achieved by placing the disks in an aqueous solution of $3.4\times10^{-4}$ M NaClO in 3 N NaOH. The solution and disks were kept at 4° C. for 5 hours and then washed thoroughly with distilled water (Sano, et al., supra). Amine group concentration was determined using a dye sorption method. Five of the disks were placed in a solution $5\times10^{-4}$ M Acid Orange 7 of pH=3 at 30° C. for five hours. The disks were then washed in $1\times10^{-3}$ N HCl to removed non-complexed dye. The complexed dye was then desorbed into a solution of $1\times10^{-3}$ N NaOH and the optical density of the resulting solution measured at 485 nm. A calibration curve for the absorption of Acid Orange 7 was made. Once the amount of dye desorbed is known the concentration of groups per unit area of treated material can be calculated.

Some of the acrylamide grafted disks were prepared for staining with toluidine blue by placing the disks in 1 M NaOH at 70° C. for 1 hour. This treatment has been shown to hydrolyze about 70% of the amide groups (Sano, et al., supra). The disks were then embedded in resin and sectioned using a microtome. Finally, the sections were stained in $5 \times 10^{-4}$ M toluidine blue to visualize the grafted area. The staining showed acrylamide grafting only on indentation surfaces 32, and not on the surface between indentations 26.

Figure 8:
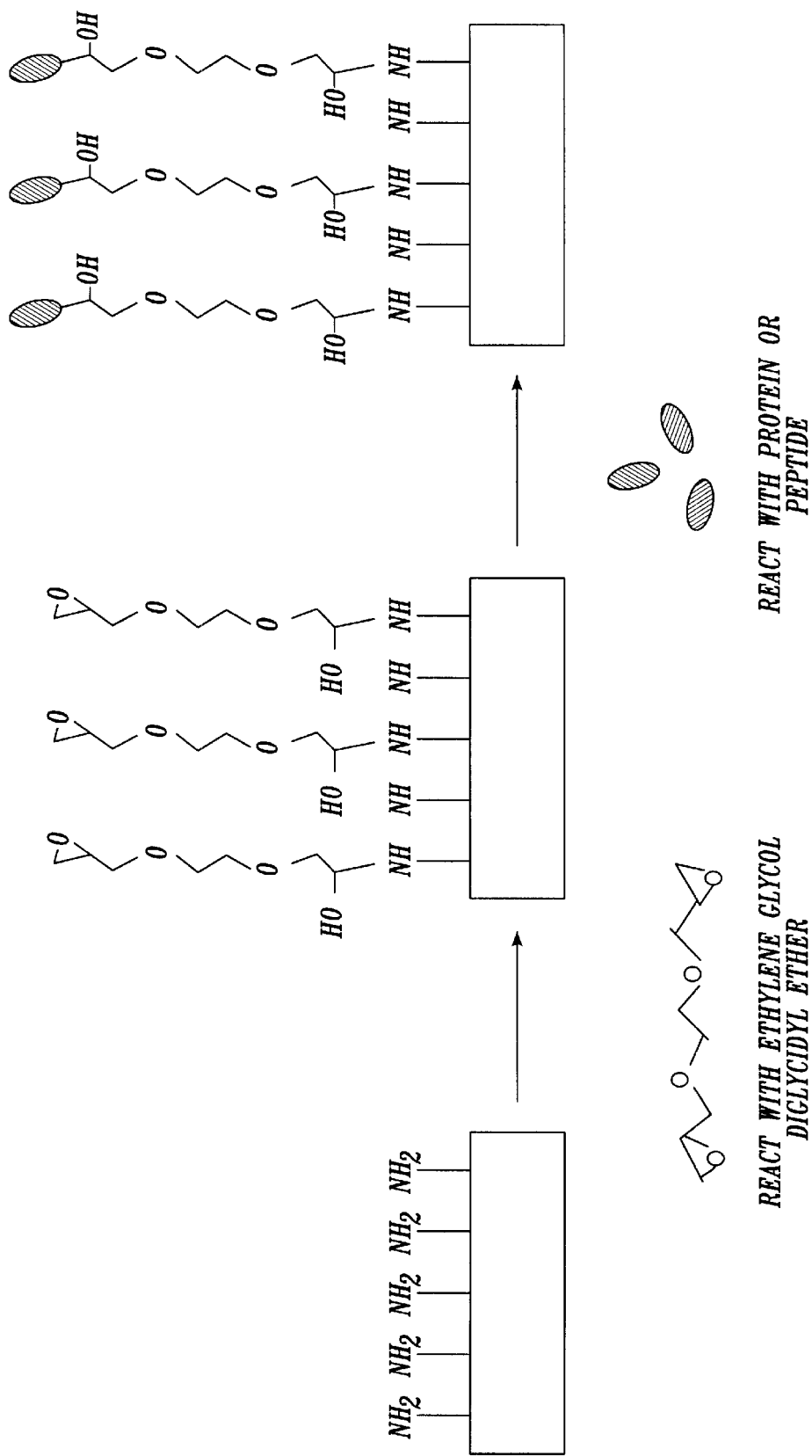
FIG. 8 shows the attachment of a protein (shaded ovals) to amine groups via an ethylene glycol diglycidyl ether linker.

The acrylamide amine groups can be used to immobilize proteins through a variety of linkers. In the studies reported in this Example, an ethylene glycol diglycidil ether (ED) was chosen as the linker since it is hydrophilic and acts as a spacer for attached proteins. The reaction sequence for attaching the linker to the amine groups of acrylamide, and then attaching a protein or peptide to the linker is shown in FIG. 8. In brief, the disks were placed in 0.57 M ED in distilled water for 10 hours at room temperature. Then the disks were washed three times with distilled water and placed in a 1 mg/ml solution of rat albumin, SPARC peptide, or an 80 µg/ml solution of thrombospondin (TSP) in PBS, pH 9.0. The disks were allowed to react at 4° C. for 20 hours with mild agitation. Following the immobilization reaction, the disks were extensively washed in PBS, pH 7.5, and then placed in a 1% solution of SDS for 24 hours to remove adsorbed protein. The disks were again washed extensively in PBS, pH 7.5, before implantation.

The immobilization of proteins to the indentation surfaces 26 was analyzed by transmission Fourier transforrn infrared spectroscopy (FTIR), Electron Spectroscopy for Chemical Analysis (ESCA), and scanning electron microscopy (SEM). ESCA was performed using a Surface Science Instruments SSX 100 spectrometer located in the National ESCA and Surface Analysis Center for Biomedical Applications (NESAC/BIO) at the University of Washington, Seattle, Wash. The spectrometer used $AlK_\alpha$ monochromatic X-rays and a low-energy flood gun for charge neutralization. Spectra were recorded with an electron take-off angle of 55° from the vertical. Wide spectra scans (150 eV pass energy) and high-resolution scans (25 eV pass energy) of the $C_{1s}$, $O_{1s}$, and $F_{1s}$ peaks were performed. A scanning electron microscope (JEOL 35C) was also used to study film topology.

As shown in Tables 1 and 2, the atomic percentage of oxygen on indentation surfaces 32 increased from 5.57 to 6.46 after oxidation of the polyethylene film with chromium oxide. The presence of silicon is most likely due to contamination.

TABLE 1

Surface composition of indentation surfaces 32 before treatment with chromium oxide.

| Element (Electron Shell) | Binding Energy(eV) | Atomic Percentage |
|---|---|---|
| Oxygen (1s) | 528.71 | 5.57 |
| Carbon (1s) | 280.87 | 92.15 |
| Silicon (2s) | 149.20 | 2.28 |

TABLE 2

Surface composition of indentation surfaces 32 after treatment with chromium oxide.

| Element (Electron Shell) | Binding Energy(eV) | Atomic Percentage |
|---|---|---|
| Oxygen (1s) | 528.90 | 6.46 |
| Carbon (1s) | 280.86 | 92.96 |
| Silicon (2s) | 149.65 | 0.58 |

Table 3 shows data characterizing the surface chemistry of polymeric layer 52 after functionalizing with amines by Hoffman degradation. Note the presence of nitrogen after Hoffman degradation (Table 3).

TABLE 3

Surface composition of polymeric layer 54 after polypropylene amine functionalization by Hofmann degradation.

| Element (Electron Shell) | Binding Energy(eV) | Atomic Percentage |
|---|---|---|
| Oxygen (1s) | 529.74 | 8.06 |
| Carbon (1s) | 281.52 | 89.69 |
| Nitrogen (1s) | 396.30 | 1.00 |
| Chlorine (1s) | 197.59 | 1.24 |

Table 4 shows data characterizing the surface chemistry of polymeric layer 54 after immobilization of protein albumin thereon. Note the increased amounts of nitrogen, oxygen and sulfur characteristic of proteins.

TABLE 4

Surface composition of polymeric layer 54 after immobilization of protein albumin thereon.

| Element (Electron Shell) | Binding Energy(eV) | Atomic Percentage |
|---|---|---|
| Oxygen (1s) | 529.45 | 11.81 |
| Carbon (1s) | 281.41 | 83.53 |
| Nitrogen (1s) | 396.60 | 3.16 |
| Sulfur (2p) | 165.62 | 0.56 |
| Silicon (2p) | 100.91 | 0.93 |

In terms of surface analysis of the laser-drilled indentations 26, it was difficult to distinguish the surface chemistry of the indentation 26 borders from the non-indented surface portion therebetween. In order to assess this, the laser drilled samples were treated with Toluidine blue, after the acrylamide grafting step. Staining with Toluidine blue showed that there was preferentially more hydrogel grafted on indented surfaces 32 than on the non-indented surface portions therebetween. This is presumably due to enhanced oxidation of indented surfaces 32 from the laser treatment.

Biological evaluation of the polypropylene disks prepared as described in this Example, and including either a four amino acid fragment of SPARC protein (i.e., "secreted protein, acidic and rich in cysteine" as described in Iruela-Arispe, M. L., et al., Mol Biol Cell, 6(3): 327–343 (1995), which publication is incorporated herein by reference), having the amino acid sequence KGHK (SEQ ID NO:1), or Thrombospondin 2 (TSP2)(see, e.g., Kyriakides T R, et al., J Cell Biol., 140(2): 419–30 (1998), which publication is incorporated herein by reference), was carried out by implantation for three weeks subcutaneously (S.C) on the front and backs of Sprague-Dawley rats.

Prior to implantation, materials were tested for endotoxin using the Limulus amebocyte lysate test (Associates of Cape Cod, Inc., Falmouth, Mass.) following the gel-clot procedure provided by the manufacturer. All surgical procedures were approved by the University of Washington Animal Care Committee. Eight Sprague-Dawley rats weighing 250 to 300 grams were used for the implantation study. The animals were first anesthetized using isoflourane gas, then shaved and prepped with betadine. Four, one-centimeter longitudinal incisions were made in the dorso-lumbar region of the animal using a scalpel. From each incision a pocket was made using blunt dissection with a hemostatic forceps. One disk was implanted subcutaneously into each of the four pockets. Care was taken to avoid contact of the disk with the edges of the incision during implantation. The assignment of implants to rats (i.e., assignment to the thrombospondin, SPARC, or control groups) was randomized. The location of each pair of implants in an animal (either left or right side of the animal) was also randomized to account for site-to-site variability. Disks with 50-micron indentations 26 were used for all the implants. The incisions were closed using surgical glue (Vetbond; 3M Corporation, St. Paul, Minn.). Three weeks after implantation, the animals were euthanized and the materials explanted with the surrounding tissue.

SPARC would be expected to promote angiogenesis and reduce fibrous capsule, while TSP-2 would be expected to reduce both measurements. As shown in Table 5, the expected trends in encapsulation and angiogenesis were observed. There were a total of 8 sites in each treatments group and also the albumin control materials.

TABLE 5

Overall mean data for the implantation study.

| Implant | Fibrous Capsule Thickness ($\mu$m) | Vessel Surface Area Per Unit Volume ($\mu m^2/10$ $\mu m^3$) | Vessel Number Per Unit Area (vessels/view) |
|---|---|---|---|
| Albumin (n = 14) | 17.1 ± 3.8 | 6.2 ± 3.0 | 4.5 ± 1.9 |
| SPARC (n = 6) | 17.8 ± 1.7 | 8.7 ± 2.9 | 5.7 ± 1.6 |
| TSP (n = 8) | 15.7 ± 2.9 | 5.7 ± 1.6 | 3.9 ± 1.3 |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An indented structure comprising:
   (a) a body defining a plurality of indentations, substantially all of said plurality of indentations comprising a layer comprising a biologically active substance; and
   (b) a body surface defined by said body, wherein each of said plurality of indentations opens onto said body surface through a plurality of openings, and wherein said biologically active substance is not substantially present on said body surface.

2. An indented structure of claim 1 wherein said indented structure is a medical device.

3. An indented structure of claim 2 wherein said indented structure is selected from the group consisting of artificial joints, vascular grafts, stents, skin substitutes, scaffolds that support tissue growth, biosensors and percutaneous devices.

4. An indented structure of claim 1 wherein said indentations are columnar.

5. An indented structure of claim 1 wherein said indentations are curved.

6. An indented struture of claim 1 wherein said indentations are grooves.

7. An indented structure of claim 1 wherein said biologically active substance is covalently attached to a layer of polymer.

8. An indented structure of claim 1 wherein said biologically active substance is selected from the group consisting of growth factors, stimulators of vasculogenesis, antibiotics and antisense oligonucleotides, or at least one functional domain of one or more of said biologically active substances.

9. An indented structure of claim 1 wherein more than 99% of the plurality of indentations comprise a surface layer comprising a biologically active substance.

10. An indented structure of claim 1 wherein less than 25% of the amount of biologically active substance present in the indented structure is present on the body surface.

11. An indented structure of claim 1 wherein less than 10% of the amount of biologically active substance present in the indented structure is present on the body surface.

12. An indented structure of claim 1 wherein less than 1% of the amount of biologically active substance present in the indented structure is present on the body surface.

* * * * *